United States Patent [19]
Pohl

[11] Patent Number: 6,080,699
[45] Date of Patent: Jun. 27, 2000

[54] HETEROGENOUS CATALYST, ITS MANUFACTURE AND ITS USE

[76] Inventor: Joachim Pohl, Warthestrasse 5A, D-14513 Teltow, Germany

[21] Appl. No.: 09/142,383

[22] PCT Filed: Mar. 12, 1997

[86] PCT No.: PCT/EP97/01279

§ 371 Date: Sep. 1, 1998

§ 102(e) Date: Sep. 1, 1998

[87] PCT Pub. No.: WO97/34695

PCT Pub. Date: Sep. 25, 1997

[30] Foreign Application Priority Data

Mar. 21, 1996 [DE] Germany .............................. 196 11 132

[51] Int. Cl.$^7$ .............................. B01J 23/70; B01J 21/04; B01J 23/02; B01J 23/58; B01J 23/00
[52] U.S. Cl. .......................... 502/303; 502/345; 502/344; 502/343; 502/330; 502/337; 502/326; 502/353; 502/305; 502/336; 502/349; 502/347; 502/355; 502/340; 502/439
[58] Field of Search .................................. 502/439, 345, 502/303, 344, 343, 330, 337, 326, 353, 305, 336, 349, 347, 355, 340

[56] References Cited

U.S. PATENT DOCUMENTS

| | | |
|---|---|---|
| 3,846,495 | 11/1974 | Svarz ....................................... 260/561 |
| 5,124,302 | 6/1992 | Lachman et al. ........................ 502/213 |
| 5,134,108 | 7/1992 | Thakur et al. ........................... 502/318 |
| 5,173,468 | 12/1992 | Boehning et al. ....................... 502/209 |
| 5,198,403 | 3/1993 | Brand et al. ............................. 502/204 |
| 5,446,004 | 8/1995 | Tenten et al. ............................ 502/312 |
| 5,609,756 | 3/1997 | Betz et al. ............................ 210/198.2 |
| 5,677,261 | 10/1997 | Tenten et al. ............................ 502/439 |
| 5,686,373 | 11/1997 | Tenten et al. ............................ 502/312 |
| 5,840,971 | 11/1998 | Gubelmann-Bonneau ............. 562/538 |

FOREIGN PATENT DOCUMENTS

| | | |
|---|---|---|
| 1 279 660 | of 0000 | Germany . |
| 8 723 | of 0000 | Germany . |
| 51-137686 | 11/1976 | Japan . |
| 61-242644 | 10/1986 | Japan . |
| WO 94/15708 | 7/1994 | WIPO . |

*Primary Examiner*—Steven P. Griffin
*Assistant Examiner*—Cynthia M Donley
*Attorney, Agent, or Firm*—Herbert Dubno

[57] ABSTRACT

A heterogeneous massive catalyst is disclosed which comprises: at least one catalytically active component in the form of solid particles and at least one catalytically inert component in the form of solid particles wherein the components are dispersed in one another, wherein the inert component has a mean particle diameter greater than the mean particle diameter of the catalytically active component, and wherein the particles of the catalytically active material are grown on the particles of the catalytically inert material as well as a process for preparing the catalyst.

25 Claims, 4 Drawing Sheets

HETEROGENOUS CATALYST, ITS MANUFACTURE AND ITS USE

This application is the National Stage of PCT/EP97/01279 filed Mar. 13, 1997.

FIELD OF THE INVENTION

The present invention relates to a process for producing a heterogeneous catalyst, which is comprised of at least one catalytically active component and at least one catalytically inert component, whereby the components are dispersed in one another.

The "mean particle diameter" or the "particle size" mentioned in this application is understood to be the $d_{50}$ value. This value is so defined that 50% of the particles in question have a smaller particle or grain diameter then the given $d_{50}$ value.

BACKGROUND OF THE INVENTION

In the production of industrially used heterogeneous catalysts, two types can be differentiated, namely supported catalysts and massive catalysts. With supported catalysts, the catalytically active material, for example, metal salts or metal oxides are applied to a catalytically inactive support, for example, aluminum oxide, by immersion or impregnation. The form and size of the support, for example, balls or tablets with dimensions of 10 to 50 mm, determine in this case, the shape and size of the finished catalyst. By contrast thereto, the massive catalyst is comprised of a powder mixture of a catalytically active and an inert mass. It has a shape and size determined by the subsequent shaping of the mixture, for example, by extruding or pelletizing.

The invention relates to massive catalysts. They are produced according to the state of the art by precipitation of a metal salt solution, filtration, drying, calcining and subsequent shaping and optionally reduction, e.g. with hydrogen.

The activity, selectivity and life of a catalyst for a given chemical composition depends to a considerable extent upon its physical structure. One understands physical structure to refer to the dispersity, the surface structure and the pore structure. Correspondingly, for many applications, a fine grained catalyst finely divided within the finished shape of the catalyzer, with a high specific surface area, is preferred.

To obtain an especially high dispersity and surface area of the massive catalyst, it is known in the art to precipitate the catalytically active metal salts together with catalytically inert components. Such catalysts are not supported catalysts but rather are considered massive catalyst which are produced by a so-called "mixed precipitation".

An example of such mixed precipitation is found in DE 39 30 298 A1. Here, a massive copper-zinc-silicate catalyst is produced by addition of a solution of copper nitrate and zinc nitrate to a solution of sodium silicate with vigorous agitation.

It is important with such mixed precipitation that there be a higher solubility product of the active component than that of the inert component at the given pH value. In this case, the inert component precipitates initially in a fine particle size, typically about 500 nm, upon which the smaller particles of the active component can grow. The larger inert particles with the smaller active particles deposited thereon, enable a fine distribution of the active component in the massive catalyst. These particles have, in addition, a high mechanical stability so that the particles of the active component cannot be readily separated from the inert component under customary conditions.

On the contrary, what is unwanted is the opposite ratio of the solubility products. In this case, initially the active components precipitate in the form of relatively large particles upon which the inert fine grained particles deposit. On the one hand, the catalytically effective surface is partly covered by the inert particles. On the other, there is a further drawback in the experimentally determinable reduction in the adhesion of the active particles on the inert particles in the mixed particles mass.

The mixed precipitation under the above mentioned desirable conditions, has several drawbacks. One is the fact that a satisfactory difference of the solubility products of active and inert components corresponding to the aforedescribed requirements only occurs in a limited range of pH values. However, the pH value changes during the precipitation so that, in many cases, only at the beginning of the precipitation, but not toward the end of precipitation, is there a sufficient difference of the solubility products of the two components.

It frequently happens that toward the end of the precipitation the solubility products of the two components become sufficiently close that both components precipitate practically simultaneously and a growth of the active component on the previous precipitated support crystallites no longer occurs.

A further disadvantage resides in the limitation of the components which can be used to those with suitable differences in the solubility products. Thus, the solubility product of the inert component must be less than $10^{-9}$. A mixed precipitation with titanium dioxide as the inert component, which has a solubility product of $10^{-5}$, and with copper as an active component, is thus not possible.

Apart from precipitation or mixed precipitation, there are in the art alternative process for producing heterogeneous massive catalysts. The requisite fine distribution of the active component is here not reached in a physical-chemical manner but rather by mechanical comminution.

Thus heterogeneous catalysts on the basis of monocrystalline alloys are produced by mechanical alloying (WO 90/09846 A1). The copper and nickel containing catalysts contain as inert components, silicon or silicon dioxide. A special advantage of these catalysts resides in their waterfree production process. For production, the corresponding metal powders are milled with high energy in a ball mill. In addition to the milling, there is a welding of the metal powder particles to one another. Responsible for the resulting alloys is a diffusion controlled solid body reaction between the thin rolled out layers. One obtains crystallite sizes below 10 nm.

The production of catalysts containing inert components corresponding to the process described at the outset, are described in addition in DE 43 08 120 A1 and WO 94/15708 A1. DE 42 09 292 A1 describes a process for processing commercially useful catalysts which is practiced in a similar manner.

According to DE 43 08 120 A1, a catalyst is produced by mixing together the starting materials forming the solid body and the catalyst forming oxidic substances, which can be apart from copper oxide or another metal oxide, at least one further metal oxide, for example, aluminum oxide, and simultaneously or subsequently comminuting the oxides to a particle size less than 10 μm mechanically. Preferably the $d_{50}$ value of the comminuted starting materials lies between 0.1 μm and 1 μm.

The comminuted starting materials according to the examples of this publication can be copper oxide and titanium oxide or copper oxide and aluminum oxide, with one being a catalytically active component and the other being a catalytically inert component. According to a preferred embodiment of the known process, the comminution is carried out with introduction of a liquid, especially water. However, separate suspensions of the catalytically active and catalytically inert components are not produced but both components are milled together with one another simultaneously. A given ratio of the particle sizes of the catalytically active and the catalytically inert components cannot be maintained in this manner. From DE 43 08 120 A1 as well as from WO 94/15708A1, numerical values of this particle size ratio cannot be deduced. If, however, a certain particle size ratio of the active and inert components is not obtained, there are the following drawbacks whose origins have been deduced by me.

The specific surface area (SA) in $m^2/g$ of ultrafine particles in the size range of 1000 mm and less depends upon the specific gravity D(in g/ml) and the mean particle diameter $d_{50}$ (in nm) and is given by the formula $SA=6000/(D \cdot d_{50})$. The specific area can have the following values at $d_{50}=500$ nm as given for several typical catalyst components:

| | |
|---|---|
| $TiO_2$ | 3.0 $m^2/g$ |
| CuO | 1.9 $m^2/g$ |
| $Cr_2O_3$ | 2.3 $m^2/g$ |
| $Al_2O_3$ | 3.0 $m^2/g$ |
| $SiO_2$ | 5.5 $m^2/g$ |
| ZnO | 2.1 $m^2/g$ |

The particles of the specifically lighter inert components have thus a greater specific area than the particles of the specifically heavier active components for a given size range. A common milling of the active and the inert components to a common particle size thus gives rise to a greater specific surface area of the inert particles relative to the active particles. A coating of the surface of the active particles with the inert particles and thus a reduction of the catalyst activity is the consequence.

Apart from this drawback, these two last mentioned publications are characterized also in that during the comminution a very high energy is applied to the starting materials. In the examples, the energy input during the milling is 30 or 150 kW per liter of reactor volume. In the preferred embodiment of the known process the energy density referred to is up to 500 kW per liter of reactor volume. With such energy inputs, there is not only a mechanical comminution but, as has been described also in DE 43 08 120 A1, a solid body reaction similar to that in the case of the already described mechanical alloying (WO 90/09846). Milling with such high energy inputs requires cooling devices which are of high apparatus cost. In the comminution of the starting materials, temperatures up to 400° C. can also arise.

In the regenerating process according to DE 42 09 292 A1, the catalysts used are also mechanically comminuted to a particle size smaller than 10 μm, preferably to reach a particle size between 0.1 μm and 4 μm. During the comminution, the catalyst is impacted with a mechanical energy with an energy density of up to 500 kW per liter of the reactor volume so as to carry out a solid body reaction. The reprocessed catalyst can be used anew to carry out reactions.

In this process, the active and inert components are comminuted together and to the same particle size so that for the reasons already mentioned, a reduced catalyst activity results.

OBJECT OF THE INVENTION

It is the object of the invention to provide a process for producing a heterogeneous catalyst of the initially described type which satisfies the following requirements. Such catalysts should be fabricated economically with components which in their soluble form have a solubility product of greater than $10^{-9}$, for example, titanium dioxide with a solubility product of about $10^{-5}$, and which, for this reason, cannot be made by precipitation or mixed precipitation. The limitation with respect to precipitation or mixed precipitation, that the solubility product of the inert component must be less than the solubility product of the catalytically active component should not intervene in the fabrication process of the invention. There should be no difficulties with disposal, after the fabrication of the catalyst of remaining heavy metal containing residues. The manufacturing process should, in addition, be carried out in a short period of time and with only a low apparatus cost. Thus in the production of the catalyst by mechanical alloying, extremely strong cooling of the mill or the attritor should not be required.

SUMMARY OF THE INVENTION

These objects are attained in a process of the type set out at the outset, in that one produces one or more suspensions of solid particles of the active component (Component (A)) and one or more suspensions of solid particles, the catalytically inert component Component (I). The mean particle diameter of the inert compound is greater than the mean particle diameter of the active component. The suspensions are combined while being subjected to ultrasound, the suspension liquid is separated off and the resulting solid particles are optionally subjected to a shaping. Preferably the mean particle diameter of the inert component is at least 1.1 times greater than the mean particle diameter of the active component, especially at least 1.5 times greater and especially preferably at least 3.5 times greater.

By contrast with the known process according to DE 43 08 120 A1, according to the invention no additional suspending agents and antistatic agents are required to maintain the solid insoluble particles in suspension and to avoid a reagglomeration of the particles. Such agents are neither required for the production of the individual components nor their combination under ultrasound conditions. Typically the suspensions according to the process of the invention have a mean density above that of water and such that the suspensions in aqueous medium first sediment after 15 to 30 min.

A reagglomeration of the particles of the entire component system, i.e. comprised of the fine particles which have been brought together of the inert and active components, is avoided by a suitable choice of the particle size ratio of active and inert components. Thereby one can achieve a strong attraction between the small and large particles but not between combined particles of the same size or particles which are not brought together. Characteristic of the process of the invention is on the one hand the good filterability of the suspension of combined particles and the high drying rate after the separation of the suspension liquid.

The possibility of operating without antistatic agents according to the invention contributes special advantages since such substances as a rule are strong catalyst poisons.

Surprisingly it has been found that it is sufficient for the suspensions of the active and inert components with the aforedescribed particle size ratio, to be combined under the effect of ultrasound to be certain that reproducible conditions are maintained for the production of catalyst precursors of high mechanical and thermal properties. The ultrasound used serves to effect uniform mixing and homogenization of the combined suspensions. The active and inert components cannot be separated from one another following the ultrasonic treatment by normal mechanical and thermal conditions. The aforementioned ratio of the mean particle diameters enables the extraordinarily fine distribution of the active catalyst component on the inert component since the fine catalytically active particles deposit securely on the larger catalytically inert particles but a coating of the surface of the active particles with inert particles does not arise.

Together with the selection of the particle size ratio of active to inert components, the use of ultrasound upon combination of the suspensions of the individual components is especially important to the invention. The ultrasound is used for mixing of the nanocrystalline solid suspension. As distinct from the use of classical stirrers or for example, propeller stirrers or blade-type stirrers, which can only mix larger units of the suspension, the ultrasound treatment enables a thorough mixing of regions in the nanometer range. If the aforedescribed particle size ratio of active and inert components is maintained, the use of ultrasound does not give rise to a demixing of the combined suspensions. If the ratio of particle sizes of inert and active components lies clearly above the range of the invention, the ultrasound breaks up the suspension and a phase separation occurs. In the opposite case in which the particle size ratio falls below the range of the invention of inert and active components, the small inert particles deposit upon the relatively larger active particle so that the catalyst is blocked and its activity is reduced.

This case arises with the simultaneous comminution of inert and active components to the same mean particle size as has been mentioned above. In the case of the ratio of particle sizes of inert and active components according to the invention, the ultrasound distributes the active component in an optimal manner with respect to the catalyst activity on the larger inert particles.

Typical of the catalyst of the invention is that the usual solvents are omitted and the catalyst is free from soluble components, for example, nitrate residues. Such components lie below the detection limits, for example, below 1 ppm. Characteristic of the invention, further, is the round shape of the primary particles visible in electron microscopy, which are deposited on one another according to the invention. A further characteristic of the catalyst of the invention is the existence of catalytically inert components with a relatively high solubility product by comparison to the process involving mixed precipitation, for example, titanium dioxide hydrate or silicon dioxide hydrate. The catalytically active and inert components are, furthermore, not alloyed with one another as is the case with the catalysts known from the above mentioned publications. Rather the invention involves a kind of adduct formation.

The fabrication process according to the invention achieves a number of advantages. In contrast to the production by means of precipitation or mixed precipitation, no liquids are produced which must be disposed of expensively. After the separation of the catalyst precursor from the suspension liquid, the suspension liquid can be used anew for the production of starting suspensions. Such a recirculation is not possible with the precipitation or mixed precipitation according to the state of the art since the solvent contains large quantities of neutral salts of materials solubilized for the precipitation. A process as is always required to eliminate the neutral salts, for example, by evaporation or distillation, lies outside the economical realm.

The fabrication process according to the invention can be carried out with apparatus of relatively low cost. Thus the starting suspensions can be subjected to milling of active or inert components in the presence of the suspension liquid whereby the suspension liquid can simultaneously serve in major part as a cooling agent. Special cooling agents as have been required in the case of mechanical alloying or with other above mentioned solid body reactions are here not required since operations are carried out with reduced energy inputs.

The active and inert components of the suspension preferably have particle sizes up to 1000 nm and especially up to 800 nm.

Preferably the suspension liquid used is water.

An especially environmentally friendly process as has already been described is achieved when, after separation of the solid particles from the suspension liquid, the suspension liquid is recycled to produce suspensions of catalytically active and/or inert components. Preferably the suspension liquid is separated by sedimentation from the massive catalyst which is produced. Only small amounts of colloidal residues of solids remain in the liquid. These residues do not disrupt the new use of suspension liquid. Only in the case of a product changeover is it also necessary to separate out even the colloidal components. These components are separated out preferably by means of ultrafiltration.

The suspension liquid can also contain soluble components which originate in the fresh raw materials used. Typically in commercially available titanium oxide and copper oxide there are small amounts of the catalyst poisons copper sulfate, titanyl sulfate/titanium sulfate. A special advantage of the process of the invention resides in the increased solubilization of these components by the effect of ultrasound and in the separation of the soluble components from the massive catalyst together with the suspension liquid before the particles are subjected to a shaping. Thus an especially high catalyst quality is obtained. Such a cleaning of the starting material is not possible by the raw material producer as a rule or is only possible at a prohibitively high cost. When, with the process of the invention, the soluble components become more strongly enriched in the circulating water, they can be separated out in a cleaning stage which is switched into the circulation. An example of such a cleaning stage is described below in an embodiment.

In an economical form of the invention, the suspension of solid particles of the catalytically active and/or inert components are produced by milling in the presence of the suspension liquid. The suspension liquid, especially water, serves to disperse and carry away the heat produced by milling.

In the production of the fine particle component, it has been found to be advantageous to mill the components in a friction mill, especially in an annular-gap mill. In an annular-gap mill, a centrally journalled milling cone is rotated in a bell shaped hollow cone. The material to be milled enters from below into the mill, is comminuted below the milling zone and the inner wall of the housing and exits at the upper part of the mill which can also be referred to as a bell mill. A special advantage of this mill is the very narrower particle size spectrum of the resulting product. It is, however, also within the scope of the invention to use other mills or other comminution apparatus for producing the powder or starting suspensions required for the production of the catalyst.

To intensify the milling effect, milling balls can additionally be introduced into the friction mill.

For the production of the starting suspension or the finely divided powder, it is proposed that the milling energy be at most 10 kW/liter of the milled volume, preferably at most 3 kW/liter. With this energy input, it is not necessary to integrate a cooling device into the mill, since the rapid flow of the suspension liquid through the mill carries off the heat so that an external cooling of the recirculated suspension liquid is sufficient. Preferably, the water in the respective circulation segments (ultrasonic treatment, sedimentation, ultrafiltration etc.) is held at room temperature. In addition, an internal cooling water circulation can be provided in the mill to eliminate minor temperature gradients.

The combination of the finely divided components can be effected in different ways within the framework of the invention. Preferably the suspensions of the finely divided components are combined under stirring, whereby the stirring energy input is especially at least 0.4 kW/l.

It is also advantageous for the suspensions of the finely divided components to be combined under the effect of ultrasound with an energy up to 4000 W/l, especially of 200 to 600 W/l, an amplitude of 100 to 300 μm and a frequency of 16 to 30 kHz.

After the separation of the suspension liquid the resulting solid particles are dried, tableted or extruded, optionally with the addition of a plastifier, for example, organic esters and/or long chain alcohols.

It is proposed, in addition, that the suspension be subjected to a spray drying and then that the resulting granulate be subjected to a thermal decomposition prior to the shaping. The spray drying as a separation between solid and liquid follows especially a separation of the greater part of the suspension liquid in a setter. The subsequent thermal decomposition is especially advantageous when one uses as starting components hydroxides and/or carbonates of the corresponding metals and which are thermally decomposed to their oxides. The shaping is preferably an extrusion.

The process according to the invention can be used to produce a large number of different catalysts. In a preferred form of the invention one utilizes as catalytically active component copper oxide (CuO) and as the inert component, titanium dioxide. These catalysts can be advantageously used for the hydrogenation of natural fats, oil and fat derivatives, for example, fatty acid methyl esters. Such a catalyst has the special advantage that the inert component titanium dioxide is of moderate price and, in addition, because of its low reactivity is especially suitable as a dispersing component in catalysts.

In general, as catalytically active component, copper oxide (CuO), metallic copper, metallic nickel, a copper-nickel alloy and/or oxides and/or mixed oxides of nickel, cobalt, vanadium, molybdenum, iron, tin, silver, chromium, yttrium, barium, lanthanum, strontium, bismuth and/or zinc and/or metallic platinum, metallic palladium and/or metallic rhenium or mixtures or alloys/compounds thereof can be used.

As inert components, especially titanium dioxide, zinc oxide, silicon dioxide, zirconium dioxide, zirconium silicate and/or aluminum oxide or a mixture/compound thereof can be used.

For the active and inert components, not only metal oxides but also hydroxides and carbonates which are decomposed in a subsequent calcination stage thermally to the corresponding metal oxide. Compounds which are generally water insoluble but thermally decomposable to oxides of these metals can be used with advantage in the process of the invention and it is proposed that water insoluble compounds thermally decomposable to the metal oxides be used as catalytically active and/or inert compounds, whereby hydroxide and carbonate are preferred.

The invention relates in addition to a heterogeneous massive catalyst which is comprised of at least one catalytically active (A) and at least one catalytically inert (I) component, whereby the components are dispersed in one another.

The previously described process conditions of the invention are satisfactory to obtain the desired catalyst in that the catalyst is characterized by particles of the catalytically inert components upon which particles of the catalytically active components grows, whereby the mean particle diameter of the inert particles is greater than the mean particle diameter of the active component. Preferably the active and inert particles have a mean particle diameter up to 1100 nm, especially up to 800 nm. It is preferred, in addition that the mean particle diameter of the inert particles be at least 1.1 times, and still more preferably at least 1.5 times and still more preferably at least 3.5 times greater than the mean particle diameter of the active component. The separate active or inert particles are characterized below as a preliminary stage of the catalyst from which the finished catalyst with the inert particles with the active particles grown thereon, is created.

In an especially preferred embodiment, the catalyst of the invention is comprised in the preliminary stage, of a catalytically active component of copper oxide (CuO) with a mean particle diameter of 200 to 500 nm and an inert component of titanium oxide with a mean particle diameter of 600 to 1000 nm.

It is proposed that further in the first stage, the catalytically active components of the catalyst consist of copper oxide (CuO), metallic nickel, metallic copper, a copper-nickel alloy and/or oxides and/or mixed oxides of nickel, cobalt, vanadium, molybdenum, iron, tin, silver, chromium, yttrium, barium, lanthanum, strontium, bismuth and/or zinc and/or metallic platinum, metallic palladium and/or metallic rhenium or mixtures or alloys/compounds thereof. These components are in part main components and in part, for example in the case of strontium, bismuth and barium, promoters.

As inert components of the catalyst, titanium oxide, zinc oxide, silicon dioxide, zirconium dioxide, zirconium silicate and/or aluminum oxide or a mixture/compound thereof can be used.

As active component and inert component, not only metal oxides can be used. In addition, the catalytically active and/or the inert components may comprise at least one water insoluble and thermally decomposable compound, decomposable to their metal oxides, especially from the group of hydroxides and/or carbonates.

The catalysts are characterized in that they can carry out, after combination, a number of reactions. Especially a catalyst according to the invention can be used for hydrogenation, hardening or oxidation, especially for the hydrogenation and hardening of natural oils, fats, fatty acids, fatty acid alkylesters and other fatty acid derivatives. Copper containing catalyst are especially suitable for example for the hydrogenation of fatty acids and fatty acid esters. Nickel containing catalysts are especially good for the hardening of natural oils, fat and fatty acids.

BRIEF DESCRIPTION OF THE DRAWING

The invention and examples are described in further detail with reference to the drawings. They show FIG. 1 a schematic illustration of the starting components as well as the finished catalyst with the particle size distribution.

DETAILED DESCRIPTION OF THE DRAWING

In all of the drawings, the same reference characters have the same significance and are thus described only once.

Figure 1:
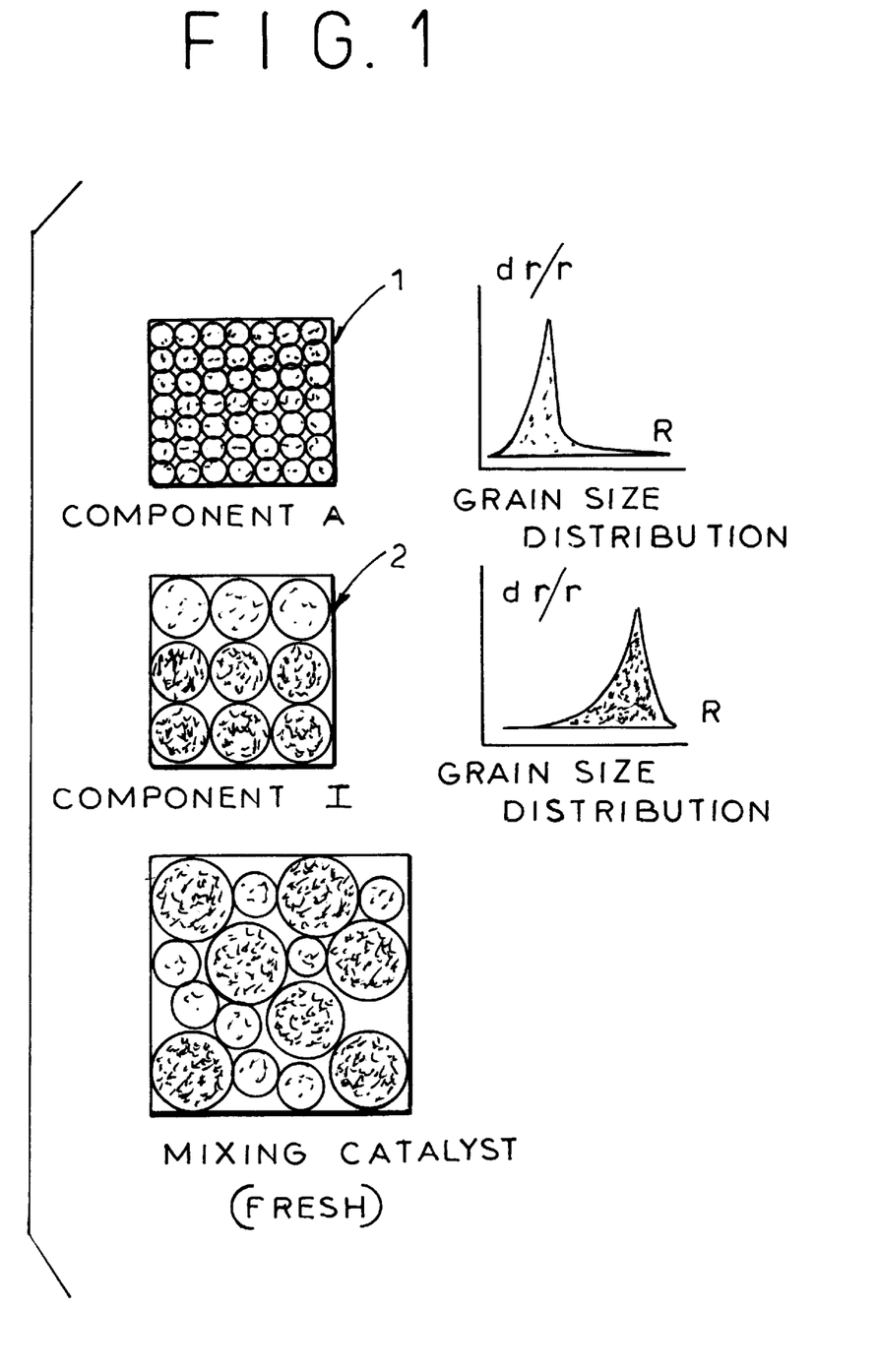

Partial illustration 1 in FIG. 1 shows schematically the finely divided particles of the catalytically active starting component A. In a corresponding way, the partial illustration 2 shows the catalytically inert component I. To the right of the partial illustrations 1 and 2 is the particle size distribution dr/r plotted as a function of the radius. Apart from the clearly higher mean particle size of the component I, it is clear that the particle size distribution of the two components A and I overlap only to a limited extent. Since these schematic diagrams will only serve to qualitatively clarify the concept of the invention, the axes are dimensionless.

In the lower part of FIG. 1, schematically a cross section through the finished catalyst of the invention has been illustrated. One can see the smaller particles of the catalytically active component A which are disposed between the larger particles of the catalytically inactive component I.

The diagram in FIG. 1 relates to a catalyst fabricated from fresh raw materials rather than a regenerated catalyst.

Figure 2:
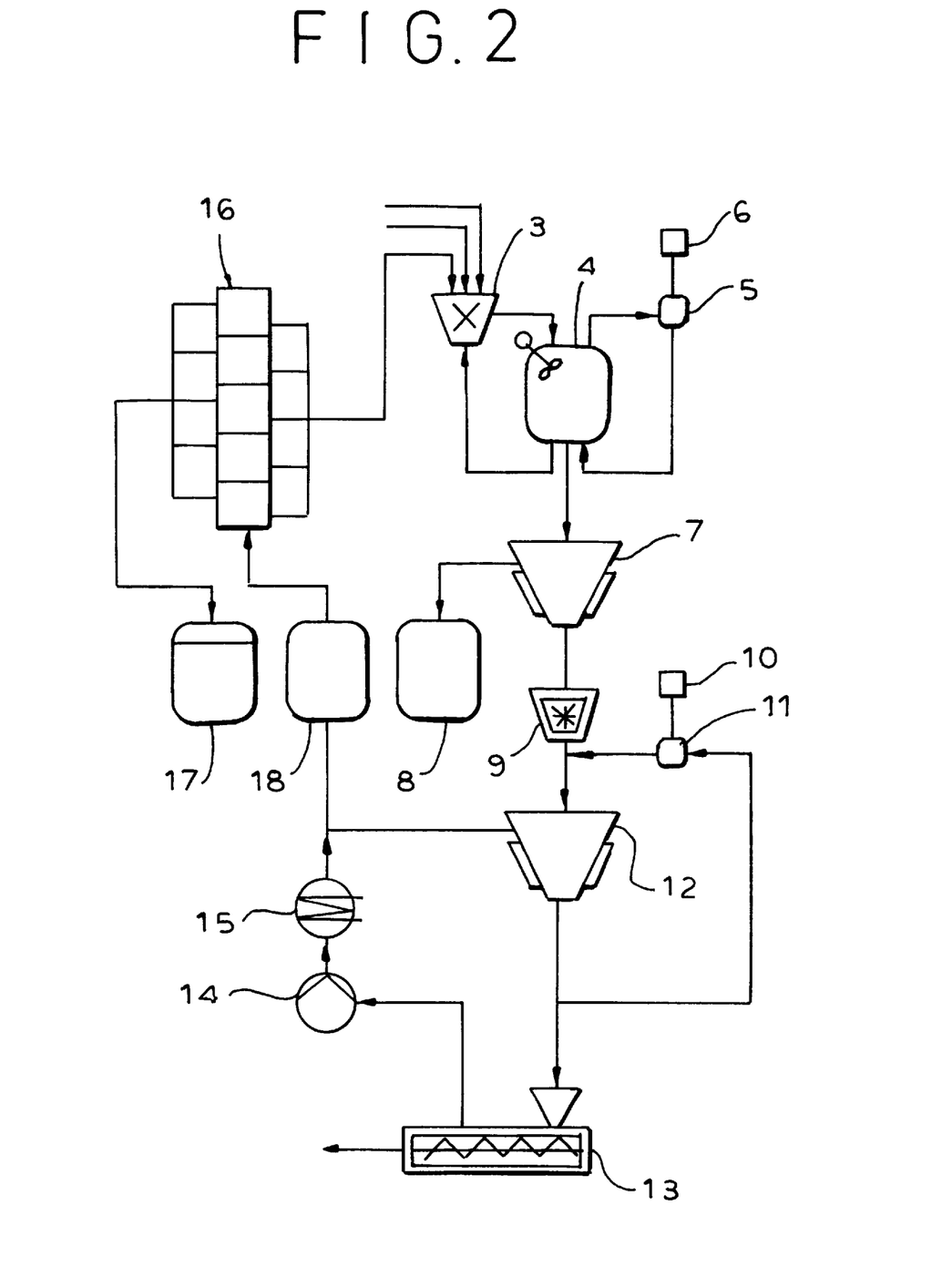
FIG. 2 is a flow diagram of the fabricating process according to the invention according to an embodiment.

In the flow diagram of FIG. 2, the fresh raw material, optionally together with secondary raw material from regenerated used catalyst, is precomminuted with recycled suspension liquid in a mill 3 and is slurried in a stirred vessel 4. The used catalyst is in this example a catalyst which has been used for the hydrogenation (hardening) of natural oils. For homogenization of the suspension, a portion of the suspension is continuously led from the stirring vessel 4 and is subjected in a container 5 to ultrasound from a first sonic force 6. The precomminution and the homogenization are carried out in a recirculation which has been illustrated in the upper part of FIG. 2.

After a first settling stage 7 in which fat adherent to the used catalyst is removed, the suspension is fed to a vessel 8, where upon the homogenized suspension is milled in an annular gap mill 9 to a particle size below 1100 nm.

In a second settling stage the suspension is sedimented and the carrier liquid is removed and recycled in the system. The finely divided suspension is then homogenized by the effect of a second ultrasonic source 10 upon the partially recycled stream passing through the vessel 11. The settling tank 12 serves in addition to stabilize the suspension and as a buffer container for the subsequent vacuum extruder 13 in which the catalyst mass is dried, compacted and pressed through a perforated nozzle. The resulting strands are subdivided in a conventional manner to a granulate.

The moist air drawn off by the vacuum pump 14 is cooled in the heat exchanger 15 and the condensed liquid is collected together with the liquid separated from the settling tank 12 in the vessel 18 and is freed from colloidal particles in an ultrafiltration apparatus 16 and then led to the container 17 where it sediments. The ultrafiltration is only required in the case of a product change to the extent that exclusively fresh catalyst raw materials and no secondary raw materials from used catalysts are employed.

The cleaned suspension liquid is recycled finally to the precomminution stage.

Figure 2A:
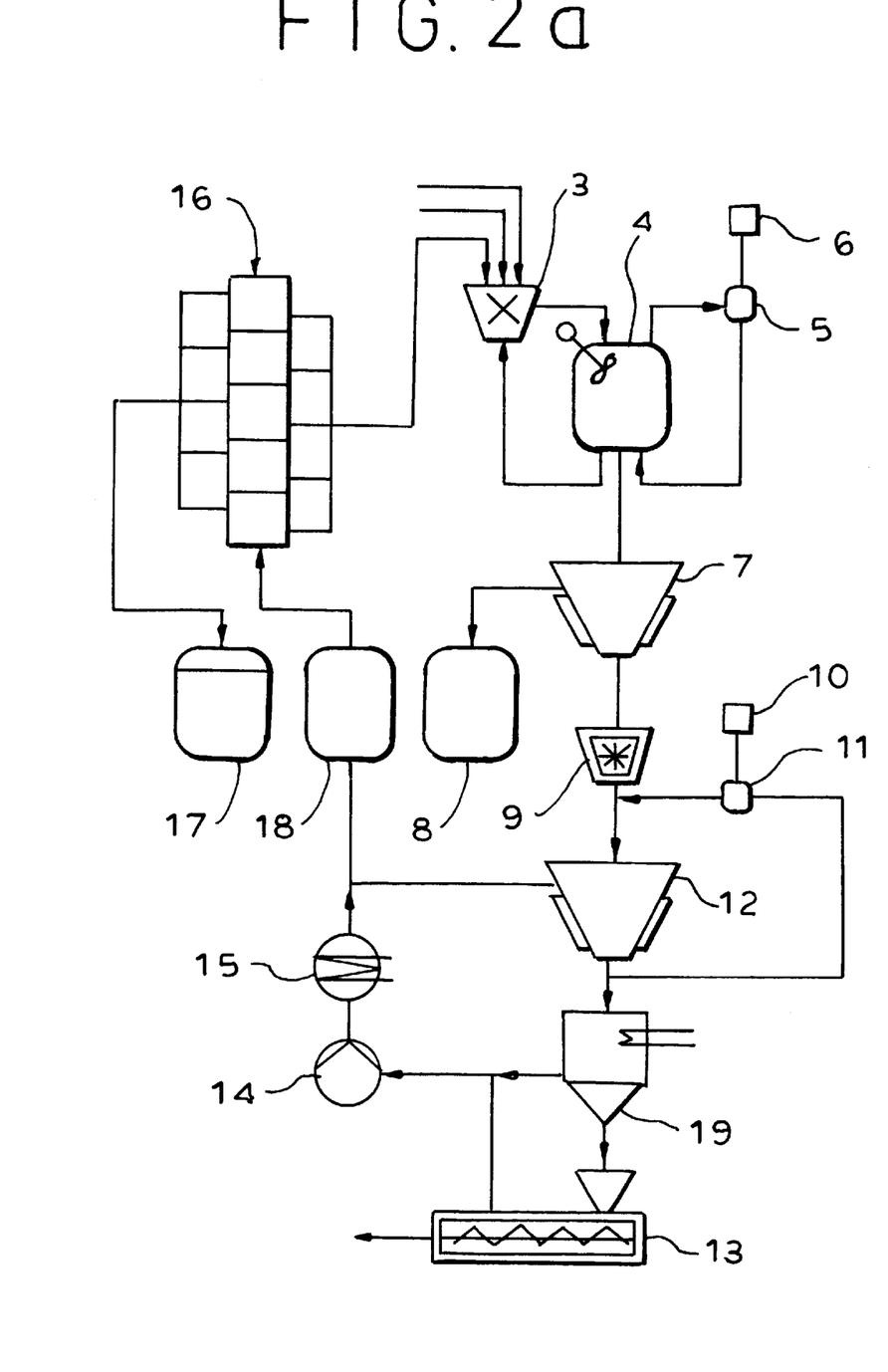
FIG. 2a is a modified flow diagram of the process according to FIG. 2.

The flow diagram according to FIG. 2a shows a modification of the process according to FIG. 2. Here, in addition, a spray drier 19 is used in which a thermal treatment and granulation also is employed.

The water removed in the spray drying is directly fed to pump 14. Only following the thermal treatment and granulation, does the shaping in extruder 13 occur. The thermal treatment is especially important when the raw materials are hydroxides, carbonates and other metal compounds which are decomposable thermally to the corresponding metal oxides. Alternatively, the thermal treatment can be carried out by calcining in a separate apparatus not shown in FIG. 2a and located between the apparatus 19 and the extruder 13.

EXAMPLE 1

1 kg of pulverulent copper oxide (from the firm Riedel de Haen, mean particle size 100 µm) is slurried with stirring with an energy input of 0.5 kW in 2 kg of the distilled water. For homogenization of the suspension, this is fed through the first ultrasonic stage 5 (power 400 kW/l amplitude 150 µm at 24 kHz with a flow rate 50/l. The homogenized suspension is thereafter comminuted in a ring gap mill 9 (type MS-12 of Fa. Fryma AG) with an energy input of 2.5 kW/l to a particle size of 400 nm and the suspension is then passed through the second ultrasonic stage 11 (circulation via a second settling stage, buffer container 12) for homogenization.

As the catalytically inert component 1.3 kg of fine grain quartz (Merck, particle size less than 200 µm) is slurried, homogenized and fed to the ring mill 9 for comminution at 2.5 kw/l to a $d_{50}$ value of 1140 nm and combined with copper oxide suspension.

The suspension mixture is homogenized in the second ultrasonic stage 11 (setting 400 w/l, amplitude 200 µm at 24 kHz) in a two-pass flow through the second ultrasonic stage. One obtains a homogenous suspension with a diameter or density ratio of $D(SiO_2)/D(CuO)=d(CuO)/d(SiO_2)=0.35$.

The carrier LAD is recycled after sedimentative separation to the process. After the thickening of the suspension to about 15 to 20 weight % in the second sedimentation stage 12, the catalyst mass is dried in a vacuum extruder 13 (of the firm Händle, Typ XC) at 10 to 20 mbar and a temperature range of 110 to 130° C. and formed into a granulate with a diameter of 2 mm.

EXAMPLE 2

1 kg of pulverulent copper oxide (from the firm Riedel de Haen, mean particle size 100 µm) is slurried as an example 1 in 2 kg of distilled water, homogenized and comminuted to a mean particle sizes of 400 nm.

The catalytically inert component was 1 kg of titanium oxide (type 3000 from the firm Kronos Titan GmbH, mean particle size 400 µm) which was suspended in the above described manner in 2 kg of distilled water homogenized with 1.5 kW/l to a mean particle size of 640 nm in the ring gap mill each in which it is comminuted and fed to the copper suspension.

The suspension mixture is homogenized in two passes in the second ultrasonic stage 11 (settings as above). One obtains a homogenous suspension with a diameter or density ratio $D(TiO_2)/D(CuO)=d(CuO)/d(TiO_2)=0.63$ which is easily separated from the liquid as a homogenous phase.

The carrier liquid is recycled to the process after separation. After taking of the suspension to about 15 to 20 weight % solids in the second settling stage 12, the catalyst mass is dried in a vacuum extruder 13 (type XC of the Firm Händle) at 10 to 20 mbar in a temperature range of 110 to 130° C., and formed into a granulate with diameter of 3 mm.

EXAMPLE 3

1 kg of pulverulent copper oxide from the first Riedel de Haen mean particle size 100 μm is slurried, homogenized and comminuted in 2 kg of distilled water to 400 nm as in examples 1 and 2. As the catalytically inert component 1.01 kg zinc oxide (from the firm Riedel de Haen, mean particle size 16 μm) was comminuted in the ring gap mill 9 with 2.0 kW/l to a mean particle size of 450 nm and fed to the copper oxide suspension.

The suspension mixture is homogenized in two bases through the second ultrasonic stage 11 (setting 400 w/l, amplitude 200 μm at 24 kHz). One obtains a homogenous suspension with a diameter or density ratio $D(ZnO)/D(CuO)=d(CuO)/d(ZnO)=0.89$ The thickening, drying and shaping were effected corresponding to the conditions in Examples 1 and 2.

ACTIVITY TESTS

The catalysts produced in Examples 1 through 3 are subjected to the nonstandard tests by users of catalysts for the hydrogenation of fatty acid methylester to the corresponding fatty alcohols (of the firm Henkel KgaA, Condea, Kao and the hydrogenation activities and selectivity were determined. The production of lauryl alcohol by the hydrogenation of lauric acid methyl ester was carried out using the new catalysts.

Test Conditions:
Reactor 1 liter Stirred autoclave
Pressure 300 bar hydrogen
Temperature 220° C.
Rotary Speed 1000 min$^{-1}$
Sample weight 300 g lauric acid methylester
15 g catalyst powder
Test Results:

| Example No. | Catalyst Type | Conversion to laurol % | By Products (%) |
|---|---|---|---|
| 1 | CuO/SiO$_2$ | 81 | 1.7 |
| 2 | CuO/TiO$_2$ | 90 | 0.4 |
| 3 | CuO/ZnO | 83 | 0.7 |
| Comparative | Copper Chromite | 87 | 0.9 |

The comparative catalyst is a commercial catalyst from the firm Südchemie which is the best commercially available catalyst for the hydrogenation of fatty acid methylesters to fatty alcohols.

The results indicate that the catalysts made in accordance with the invention have at least the same activity and selectivity as a very good commercial catalyst. By contrast with the latter, the catalysts of the invention are fabricated much more economically in a more environmentally sound manner.

In the case of CuO/TiO$_2$ catalysts both the activity and selectivity are clearly greater than the values for the commercial catalyst.

Figure 3:
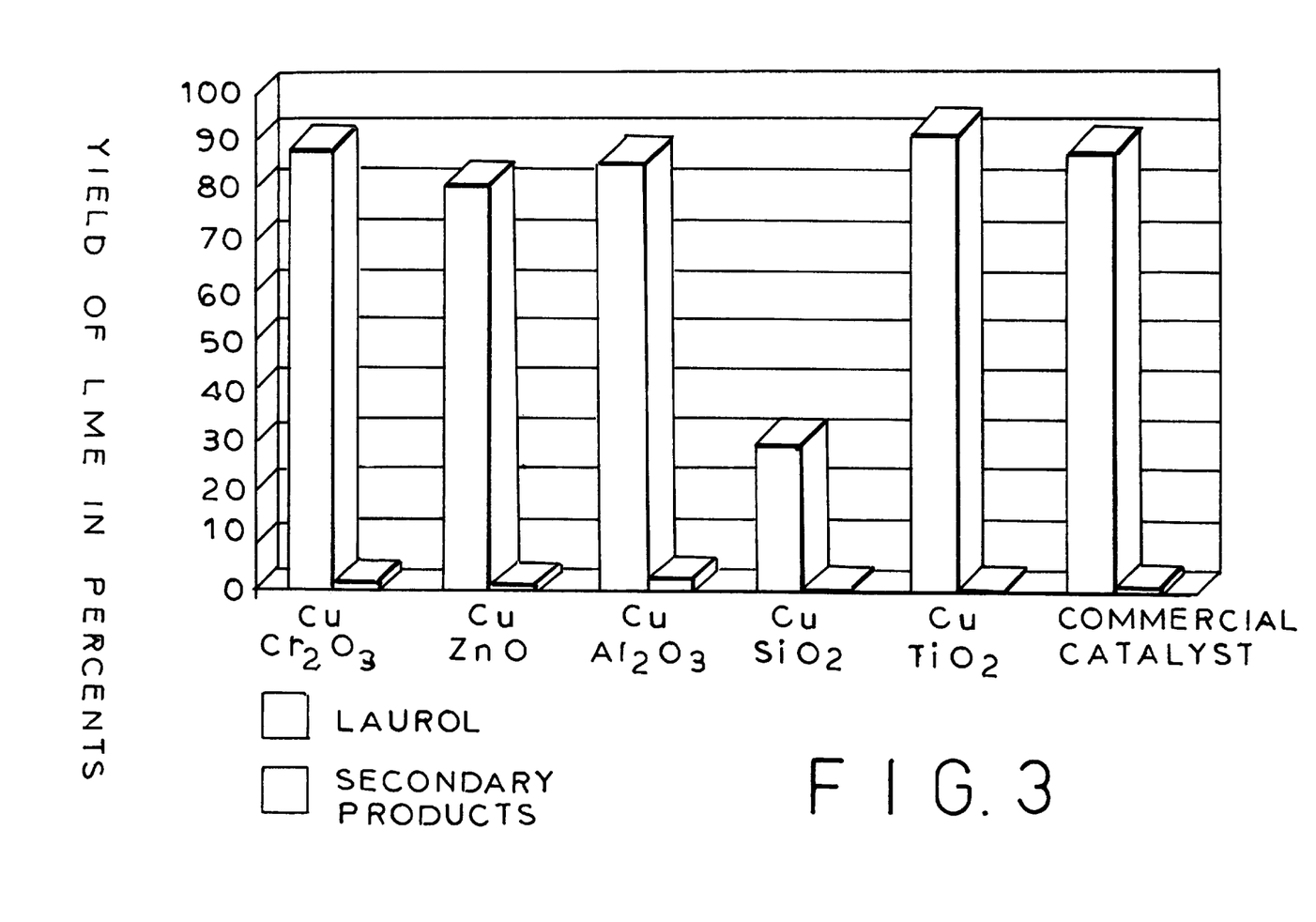
FIG. 3 shows activities of different catalysts according to the invention as well as the catalyst state of the art shown in a diagram.

In FIG. 3, the results of activity tests with several catalysts according to the invention as well as the aforementioned commercial catalyst (copper chromite) are collected.

Clearly observable is the high quality of the catalyst made according to the invention.

| REFERENCE CHARACTER LIST | |
|---|---|
| 1 | Partial Image |
| 2 | Partial Image |
| 3 | Mill |
| 4 | Stirred Vessel |
| 5 | Container |
| 6 | Ultrasonic source |
| 7 | Settling stage |
| 8 | Container |
| 9 | Ring Gap Mill |
| 10 | Ultrasonic source |
| 11 | Container |
| 12 | Settling Tank |
| 13 | Vacuum Extruder |
| 14 | Vacuum Pump |
| 15 | Heat Exchanger |
| 16 | Ultrafiltration Unit |
| 17 | Container |
| 18 | Container |
| 19 | Spray Dryer |

What is claimed is:

1. A process for producing a heterogeneous massive catalyst wherein the catalyst comprises at least one catalytically active component in the form of solid particles and at least one catalytically inert component in the form of solid particles wherein the components are dispersed in one another and wherein the inert component has a mean particle diameter greater than the mean particle diameter of the catalytically active component, which comprises the steps of:

(a) producing in a suspension liquid at least one suspension of solid particles of the catalytically active component and in a suspension liquid at least one suspension of solid particles of the catalytically inert component;

(b) combining the suspension of the solid particles of the catalytically active component in the suspension liquid and the suspension of the solid particles of the catalytically inert component in the suspension liquid and subjecting the combined suspensions to ultrasound; and (c) separating the suspension liquid from the solid particles in the combined suspension, said solid particles forming the heterogeneous massive catalyst.

2. The process for producing a heterogeneous massive catalyst defined in claim 1 wherein the catalytically inert component has a mean particle diameter at least 1.1 times greater than the mean particle diameter of the catalytically active component.

3. The process for producing a heterogeneous massive catalyst defined in claim 1 wherein the catalytically active component and the catalytically inert component have particle sizes up to 1100 nm.

4. The process for producing a heterogeneous massive catalyst defined in claim 1 wherein according to step (a) water is used as the suspension liquid.

5. The process for producing a heterogeneous massive catalyst defined in claim 1 which further comprises after separating the solid particles from the suspension liquid according to step (c), recycling the suspension liquid to step (a) to produce more suspensions of catalytically active component or catalytically inert component.

6. The process for producing a heterogeneous massive catalyst defined in claim 1 wherein according to step (a) the suspensions of the solid particles of the catalytically active component and of the catalytically inert component are produced by milling said components in the presence of the suspension liquid.

7. The process for producing a heterogeneous massive catalyst defined in claim 6 wherein the catalytically active component and the catalytically inert component are milled separately in a friction mill having milling balls.

8. The process for producing a heterogeneous massive catalyst defined in claim 7 wherein additional milling balls are introduced.

9. The process for producing a heterogeneous massive catalyst defined in claim 6 wherein the milling is carried out at a power of at most 10 kw/l of milled product volume.

10. The process for producing a heterogeneous massive catalyst defined in claim 1 wherein according to step (b) the suspensions of the catalytically active component and the catalytically inert component are combined under stirring at a power of at least 0.4 kw/l.

11. The process for producing a heterogeneous massive catalyst defined in claim 1 wherein according to step (b), ultrasound is applied with a power up to 4000 w/l.

12. The process for producing a heterogeneous massive catalyst defined in claim 1 wherein following step (c), the solid particles obtained are dried, tableted or extruded.

13. The process for producing a heterogeneous massive catalyst defined in claim 1 wherein following step (c), the solid particles obtained are subjected to spray-drying, granulating, thermal decomposing and shaping.

14. The process for producing a heterogeneous massive catalyst defined in claim 1 wherein CuO is used as the catalytically active component and titanium dioxide is used as the catalytically inert component.

15. The process for producing a heterogeneous massive catalyst defined in claim 1 wherein the catalytically active component is selected from the group consisting of CuO, metallic copper, metallic nickel, a copper-nickel alloy, oxides of nickel, cobalt, vanadium, molybdenum, iron, tin, silver, chromium, yttrium, barium, lanthanum, strontium, bismuth, zinc and a mixed oxide thereof, metallic platinum, metallic palladiom, metallic rhenium, and mixtures and alloys thereof.

16. The process for producing a heterogeneous massive catalyst defined in claim 1 wherein the catalytically inert component is selected from the group consisting of titanium dioxide, zinc oxide, silicon dioxide, zirconium dioxide, zirconium silicate, aluminum oxide, and mixtures thereof.

17. The process for producing a heterogeneous massive catalyst defined in claim 1 wherein as the catalytically active component and as the catalytically inert component, water insoluble compounds thermally decomposable to their metal salts are used.

18. A heterogeneous massive catalyst which comprises
at least one catalytically active component in the form of solid particles and at least one catalytically inert component in the form of solid particles wherein the components are dispersed in one another, wherein the inert component has a mean particle diameter greater than the mean particle diameter of the catalytically active component, and wherein the particles of the catalytically active material are grown on the particles of the catalytically inert material.

19. The heterogeneous massive catalyst defined in claim 18 wherein the particles of catalytically active component and the particles of catalytically inert component have a mean particle diameter of up to 1100 nm.

20. The heterogeneous massive catalyst defined in claim 18 wherein the mean particle diameter of the catalytically inert particles is at least 1.1 times greater than the mean particle diameter of the catalytically active particles.

21. The heterogeneous massive catalyst defined in claim 18 wherein the catalytically active component is initially CuO having a mean particle diameter of 200 to 500 nm and the catalytically inert component is titanium dioxide having a mean particle diameter of 600 to 1000 nm.

22. The heterogeneous massive catalyst defined in claim 18 wherein the catalytically active component is selected from the group consisting of initially CuO, metallic copper, metallic nickel, a copper-nickel alloy, oxides of nickel, cobalt, vanadium, molybdenum, iron, tin, silver, chromium, yttrium, barium, lanthanum, strontium, bismuth, zinc and a mixed oxide thereof, metallic platinum, metallic palladium, metallic rhenium, and mixtures and alloys thereof.

23. The heterogeneous massive catalyst defined in claim 18 wherein the catalytically inert component is selected from the group consisting of titanium dioxide, zinc oxide, silicon dioxide, zirconium dioxide, zirconium silicate, aluminum oxide, and mixtures thereof.

24. The heterogeneous massive catalyst defined in claim 18 wherein the catalytically active component and the catalytically inert component are water insoluble compounds thermally decomposable to their metal salts.

25. The use of a catalyst according to claim 18 for the hydrogenation, hardening or oxidation of a natural oil, fat, fatty acid, fatty acid alkyl ester or a derivative thereof.

* * * * *